(12) United States Patent
Marko et al.

(10) Patent No.: US 6,443,947 B1
(45) Date of Patent: Sep. 3, 2002

(54) DEVICE FOR THERMAL ABLATION OF A CAVITY

(76) Inventors: Alexei Marko, 1-108 West 14th Ave, Vancouver, B.C. (CA), V5Y 1W9; Ian McDougall, 821 East 17th St., North Vancouver, B.C. (CA), V7L 2X2; Douglass Yackel, 15717 20th Ave., White Rock, B.C. (CA), V4A 4A7; Monty Bruce, #1-6686 Main St., Vancouver, B.C. (CA), V5X 3H2

(*) Notice: Subject to any disclaimer, the term of this patent is extended or adjusted under 35 U.S.C. 154(b) by 0 days.

(21) Appl. No.: 09/516,306

(22) Filed: Mar. 1, 2000

(51) Int. Cl.[7] ............................................... A61B 18/04
(52) U.S. Cl. ............................ 606/28; 606/31; 607/105
(58) Field of Search ............................. 606/27, 28, 30, 606/31; 607/104, 105, 113

(56) References Cited

U.S. PATENT DOCUMENTS

| | | |
|---|---|---|
| 3,924,628 A | 12/1975 | Droegemueller |
| 4,949,718 A | 8/1990 | Neuwirth |
| 4,979,948 A | 12/1990 | Geddes |
| 5,084,044 A | 1/1992 | Quint |
| 5,159,925 A | 11/1992 | Neuwirth |
| 5,248,312 A | 9/1993 | Langberg |
| 5,277,201 A | 1/1994 | Stern |
| 5,433,708 A | 7/1995 | Nichols |
| 5,437,629 A | 8/1995 | Goldrath |
| 5,449,380 A | 9/1995 | Chin |
| 5,451,208 A * | 9/1995 | Goldrath .................... 607/105 |
| 5,460,628 A | 10/1995 | Neuwirth |
| 5,501,681 A | 3/1996 | Neuwirth |
| 5,542,928 A | 8/1996 | Evans |
| 5,571,153 A | 11/1996 | Wallsten |
| 5,575,788 A | 11/1996 | Baker |
| 5,693,080 A | 12/1997 | Wallsten |
| 5,720,719 A | 2/1998 | Edwards |
| 5,800,493 A | 9/1998 | Stevens |
| 5,827,269 A | 10/1998 | Saadat |
| 5,827,273 A | 10/1998 | Edwards |
| 5,868,735 A | 2/1999 | Lafontaine |
| 5,879,347 A | 3/1999 | Saadat |
| 5,891,094 A | 4/1999 | Masterson |
| 5,891,134 A | 4/1999 | Goble |
| 5,954,714 A | 9/1999 | Saadat |
| 5,956,464 A | 9/1999 | Madni |
| 5,957,962 A | 9/1999 | Wallsten |
| 6,139,570 A * | 10/2000 | Saadat et al. ................ 607/105 |

FOREIGN PATENT DOCUMENTS

| | | |
|---|---|---|
| WO | WO 94/07445 | 4/1994 |
| WO | WO 94/21202 | 9/1994 |
| WO | WO 99/60960 | 12/1999 |

* cited by examiner

Primary Examiner—Linda C. M. Dvorak
Assistant Examiner—Daniel M. Ruddy
(74) Attorney, Agent, or Firm—ipsolon LLp

(57) ABSTRACT

An apparatus and method for causing necrosis of tissue and specifically intended for thermal ablation of the uterine cavity to cauterizing the endometrial tissue. The apparatus includes a liquid-tight, liquid filled system having a distal flexible member; a proximal flexible member; and a catheter joining and providing a liquid path between these distal and proximal members. The apparatus further includes a pressurizable pneumatic chamber into which the proximal flexible member is inserted and a means to controllably heat the contents of the pneumatic chamber. The system operates to: first withdraw substantially all of the liquid into the proximal flexible member contained within the pressurizable pneumatic chamber; second to heat this liquid to a temperature such that it can cause tissue necrosis; and third to force the heated liquid from the proximal flexible member into the distal flexible member where it is maintained for a predetermined time and at a predetermined pressure. Where this distal member has been inserted into a uterine cavity or is otherwise is in contact with living tissue, the presence of the heated liquid results in tissue necrosis and cauterization.

10 Claims, 5 Drawing Sheets

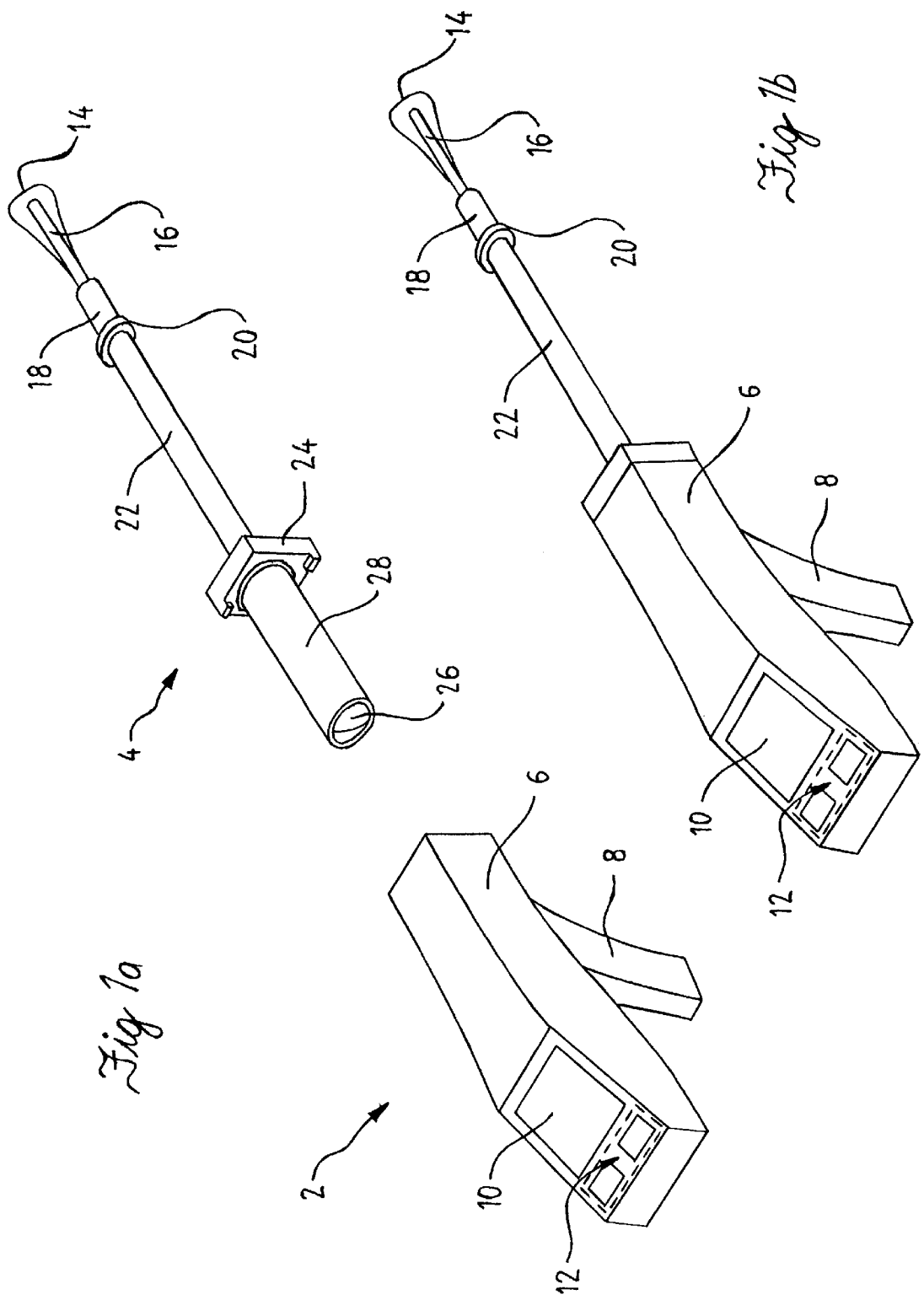

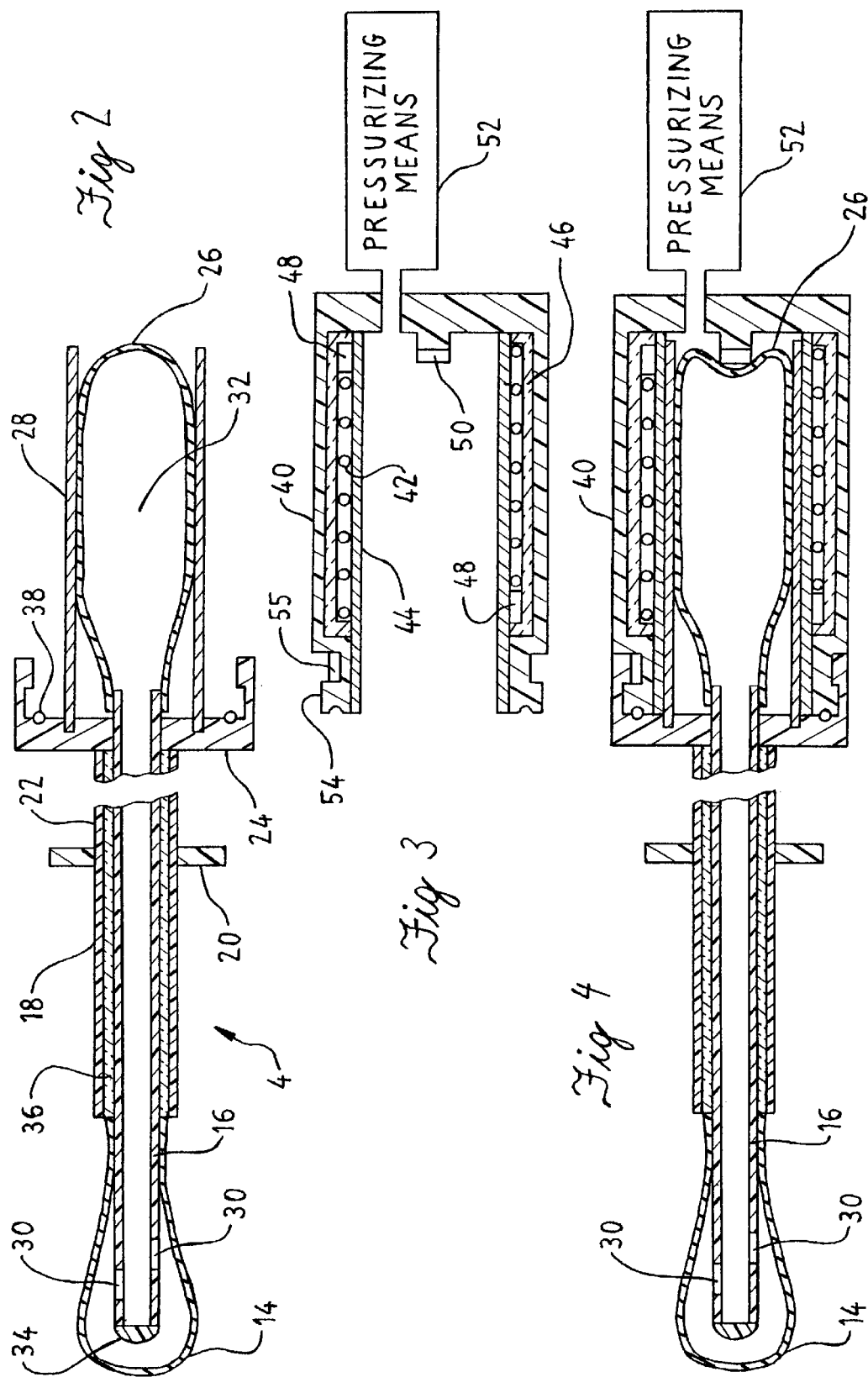

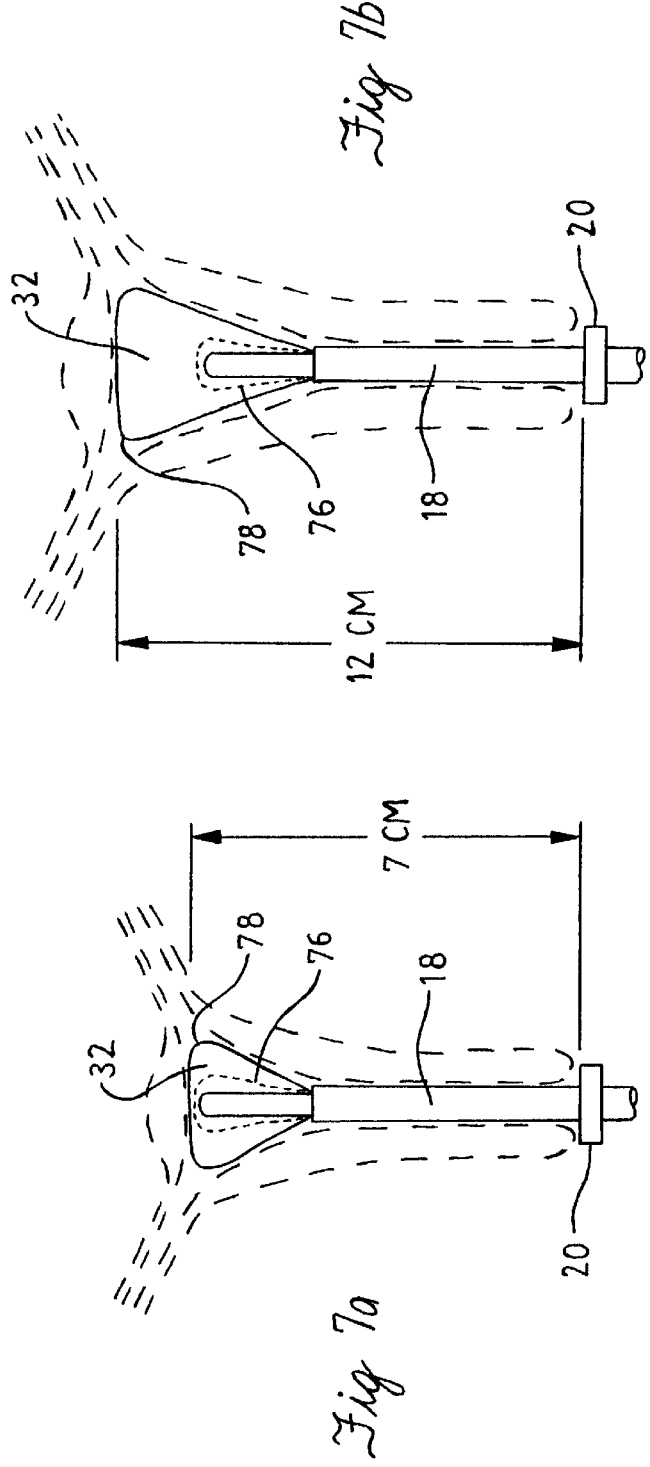
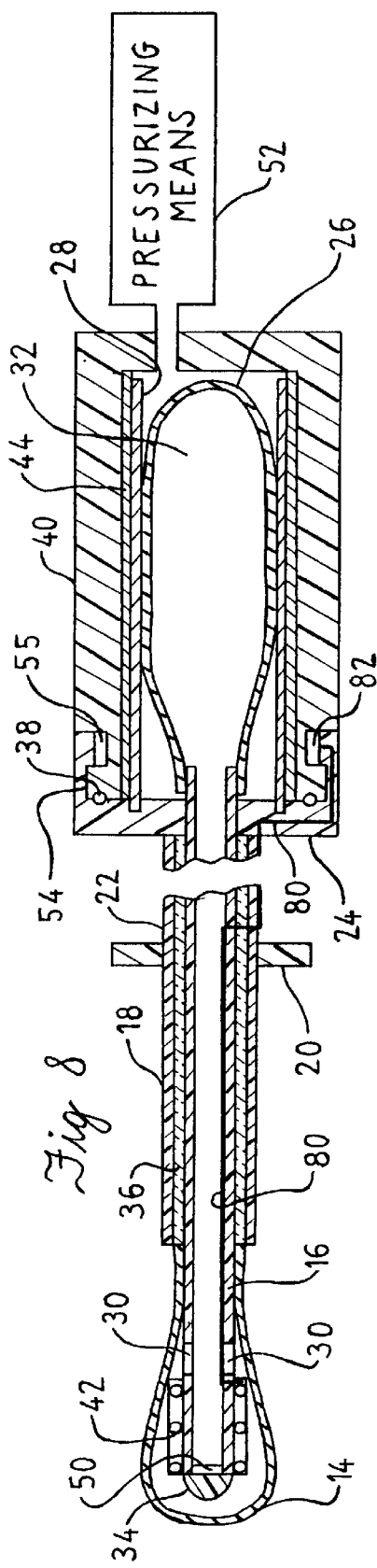

DEVICE FOR THERMAL ABLATION OF A CAVITY

TECHNICAL FIELD

The disclosed invention relates to an apparatus or device for effecting hyperthermia in a body cavity or duct. More specifically, the invention relates to apparatus and methods using a balloon or similar flexible bladder which is inserted into the uterus and filled with a heated liquid at a known pressure and for a known time in order to cauterize ("ablate") the endometrium of the uterus. This method of treatment is known as "thermal balloon ablation".

BACKGROUND AND SUMMARY OF THE INVENTION

Medical treatments involving ablation of the endometrium of the uterus are well known in the prior art. The endometrium is the portion of the uterine lining to which an embryo normally attaches and is responsible for the menstrual cycles. Such ablation treatments typically involve either the direct or indirect application of heat or cold to the endometrial tissue. Commonly, ablation devices and techniques have been used to treat menorrhagia (a condition of excessive menstrual bleeding) by cauterizing, or inducing necrosis of the endometrial lining. This cauterization prevents further proliferation of the endometrium and may result in permanent relief of menorrhagia symptoms.

Apparatuses for thermal balloon ablation are well known in the prior art. For applications to treat the endometrium of the uterus, thermal balloon ablation apparatuses typically comprise a distensible balloon which is inserted into the uterus through the external opening of the cervix. The balloon is then inflated with a liquid to expand the balloon such that it is in contact with substantially all of the uterine cavity. This liquid is then heated to a controlled temperature by a heating element within the balloon and the liquid is maintained at this temperature for a predetermined period of time. After this period of time has elapsed, the liquid is withdrawn and the balloon removed from the uterus. The heat energy which is transferred from the liquid filled balloon to the surrounding tissues of the uterus causes the desired cauterization of the endometrium. There are many examples of such devices in the prior art, for example those disclosed by Stevens et al—U.S. Pat. No. 5,800,493, and Wallsten et al—U.S. Pat. Nos. 5,693,080 & 5,571,153.

Typically the volume of liquid required to inflate the balloon ranges between 5 ml and 30 ml and is dependent on the natural volume of the uterine cavity and the liquid pressure. According to studies published in the medical literature, the liquid pressure should not exceed 180 mmHg applied to the uterine cavity walls above which there is risk of mechanical damage to the deeper tissue of the uterus.

Variations on thermal balloon apparatuses and methodologies include cryogenic apparatuses which use cooled liquid rather than heated liquid to achieve necrosis of the tissue (such as that disclosed by Lafontaine et al—U.S. Pat. No. 5,868,735) and apparatuses in which heated liquid is circulated through the uterus without the benefit of a flexible balloon to contain the liquid (such as that disclosed by Goldrath—U.S. Pat. No. 5,437,629).

A variety of alternatives to thermal balloon ablation are known for cauterization of endometrial tissue. These includes the use of microwave, RF, laser, electrical current or similar energy sources to heat a surgical probe inserted through the cervix and which is manipulated by means of direct hysteroscopic visualization. These devices typically require a highly skilled operator and produce treatment results which are more variable than those which can be achieved through thermal balloon ablation techniques. Such alternative ablation techniques also pose higher risk of perforating the uterus, normally require use of general anesthesia, and have a higher incidence of post-operative complications than thermal balloon ablation techniques.

In spite of the potential advantages of thermal balloon ablation techniques over alternative treatment methodologies, problems with the thermal balloon ablation apparatuses in the prior art have prevented such devices from being adopted widely for use in the treatment of menorrhagia.

Thermal balloon ablation systems in the prior art typically rely on heating elements located within the balloon. During heating, these devices often develop temperature gradients in the liquid which can result in uneven treatment of the endometrial surface. Typically the observed effect is to over-treat the area of the endometrium directly above the heating element and under-treat the area of the endometrium located directly below. This effect is magnified if the heating element within the balloon is inserted at an angle relative to the anterior/posterior plane of the uterus such that after inflation the heating element is located closer to the anterior wall of the balloon. Placement of the heating element relative to the balloon walls is difficult to control in practice. To reduce this problem, some inventions in the prior art include provision of an impeller, reciprocating piston or similar mechanical means to stir the liquid during heating (such as those disclosed by Neuwirth et al—U.S. Pat. No. 5,460,628 and Saadat et al U.S. Pat. No. 5,827,269) or utilize balloons which allow injection and re-circulation of heated liquid via multiple lumens, typically an "intake" lumen and an "exhaust" lumen (such as that disclosed by Lafontaine et al—U.S. Pat. No. 5,868,735). Furthermore, pulsing the liquid pressure is an alternative means to achieve more uniform mixing of the liquid (as described by Wallsten et al U.S. Pat. No. 5,957,962). However, such circulating methodologies add cost and complexity to the apparatus and the ability to achieve desired temperature uniformity depends among other factors on the volume of liquid within the balloon.

Thermal balloon ablation devices in the prior art such as that disclosed by Stevens et al—U.S. Pat. No. 5,800,493 have also relied on the operator to provide the liquid for inflation of the balloon and heating. This has limited the variety of liquids to those typically found in a clinical environment (e.g. D5%W or saline). Such liquids are generally water based and therefore cannot be heated above approximately 100 C., at which temperature these solutions begin to boil at sea level. Heating liquid to the boiling point can result in a dangerous increase in balloon volume due to expansion of gas and in uneven treatment since the presence of this gas pockets in the balloon act to thermally insulate the adjacent tissue. The maximum temperature limitation of these liquids has resulted in relatively long treatment times; it is well established in the research and in clinical practice that it requires in approximately 8 minutes to cauterize the endometrium by thermal balloon ablation using liquid temperatures of 85 C. Furthermore, the use of liquid temperatures in the range of 70–90 C. makes the use of liquid heating means external to the uterus or balloon ineffective since in this temperature range there is insufficient heat energy contained within the volume of liquid within the uterus to adequately cauterize the endometrium. In devices that employ heating means external to the balloon in the uterus and which use liquid temperatures below 100 C. (such as that disclosed by Chin U.S. Pat. No. 5,449,380) it is generally necessary to continuously circulate the liquid between the balloon and the external heating means in order to maintain an elevated liquid temperature within the uterus and to achieve the desired treatment. In addition, devices with heating elements located in the balloon within the uterus prohibit the use high viscosity liquids (such as 100% Glycerin) which resist flow at ambient temperatures but once heated become less viscous and can readily flow through a catheter to inflate a balloon placed in the uterus.

Systems which require the operator to supply the inflation liquid are also complicated for the operator to use. It is necessary for the operator to obtain a source of sterile liquid, inject the liquid into the system, check for leaks, purge gas or excess liquid from the system, and then dispose of the heated liquid after treatment. This process also compromises the sterility of the system since there is potential for non-sterile or contaminated liquid to circulate within the balloon. In the event of a balloon leak or rupture, this non-sterile liquid is released into the uterine cavity and could result in infection.

Devices in the prior art typically rely on mechanical actuators, syringes, or liquid pumps which come into contact with the treatment liquid in order to control inflation and pressurization of the balloon, these can be expensive, unreliable, and subject to contamination. Often these systems require the operator to manually inject liquid to fill the balloon. Furthermore such systems (such as that disclosed by Stevens et al—U.S. Pat. No. 5,800,493) typically have expensive disposable components as these components often include hoses, valves, connectors, electrical wiring, syringes, and heating elements which must be disposed of after each use. Wallsten et al have attempted to address this problem in the invention disclosed in U.S. Pat. No. 5,957,962 in order to provide an inexpensive disposable component however the described system still requires the addition of liquid from an external source, purging of gas from the system and relies on a mechanical apparatus and actuators to inject and remove liquid from the treatment balloon.

Often it is difficult for the operator to control inflation pressure and there is not adequate means to control this pressure in response to changes in uterine volume during treatment (typically the uterus relaxes and expands as treatment progresses and therefore it is desirable to increase the volume of liquid in the balloon to maintain a constant inflation pressure). Wallsten et al—U.S. Pat. No. 5,693,080 discloses apparatus intended to allow automated control of inflation pressure through mechanical actuation of syringes or similar means however this is costly and does not allow fine control of pressures. Wallsten et al further disclose a means for providing overpressure relief in the event of a increase in balloon pressure such as that which might be caused by a sudden contraction of the uterus during treatment however this does not provide a practical or inexpensive means for automated control of balloon inflation, deflation, and liquid pressure.

Prior art devices also rely on the operator to sound the depth of the uterus then insert a catheter or treatment element to a depth of no greater than the previously sounded depth. This requires effort on the part of the user to measure depth and observe insertion depth as marked on the treatment device. There is a danger of perforating the uterus by over-inserting the catheter if the clinician does not perform this operation properly.

In providing thermal balloon ablation treatment, it is desirous to: provide uniform cauterization of the endometrial tissue; ensure that any material which can potentially come into contact with the patient is sterile; provide the treatment in as short a period of time as possible; deliver the treatment in a manner which does not depend on the skill level of the operating clinician; and minimize the cost of any disposable components associated with the treatment apparatus. It is further desirable to avoid cauterization of the cervical canal during treatment, and to minimize the risk of perforation of the uterus when the balloon is inserted through the cervical opening or during the treatment period.

Ideally the device should be simple for the operator to use and should require minimal preparation for use by the operating clinician.

Accordingly, the present invention provides an apparatus for causing necrosis of a body cavity or duct, specifically the uterus, said apparatus comprising:

a disposable portion of the apparatus comprising a sealed system consisting of a liquid within said sealed system, an elongated distal section with a flexible balloon (or bladder) attached to it, a proximal flexible balloon (or bladder), and a means for connection to a permanent non-disposable apparatus;

a means for heating said liquid; and a permanent non-disposable apparatus comprising, a pneumatic pressurizing means for initiating flow of the liquid within said sealed system of the disposable portion of the apparatus, connection means for said disposable portion to permanent portion, and a controlling means for heating, pneumatic pressure, and time.

An object of the invention is to provide an apparatus which furnishes a means for shortened treatment time by incorporating a sealed disposable component containing a volume of liquid provided by the manufacturer. A liquid filled and sealed disposable apparatus provides one advantage as it allows the use of liquids which are not typically encountered in a clinical environment and which can be heated to temperatures in excess of 100 C. without boiling (for example 100% Glycerin). This allows improved cauterization of the endometrial lining of the uterus and shortens treatment times from 8 minutes at 85 C. to approximately 1.5 minutes at 165 C. Furthermore, by pre-heating the liquid external to the patient, high viscosity liquids (such as 100% Glycerin) can be used which flow readily at higher treatment temperatures. Because of the high viscosity at ambient temperatures, such liquids could not be readily utilized in apparatus where the heating means is located inside the balloon which is inserted into the uterus.

Another object of the invention is to provide a means of ensuring uniform treatment of the uterine cavity. The apparatus achieves the objective by injecting a pre-heated, isothermal volume of liquid into the distal flexible bladder within uterine cavity. Therefore at the time of injection into the uterus, all areas of the uterus are contacted with a uniform high temperature (approximately 165 degrees Celsius) liquid.

Another objective of the apparatus is to provide a low cost, easy to use system, that is safe and effective. The described apparatus provides for improved ease of use and reduced costs by using a disposable component comprising primarily: two flexible enclosures joined by a liquid path and containing a liquid; and a fitting which permits the proximal flexible enclosure to be sealed inside the re-usable pneumatic chamber. By using a sealed system containing a bolus of liquid, the operator simply installs the disposable cartridge and initiates heating. There is no need to source liquid, fill the system, or purge gas from the system. This makes the apparatus much easier to use and improves patient safety by ensuring sterility of the system. Since the liquid is contained in a sealed system and is driven by pneumatic means, in the event of a balloon rupture only sterile liquid can be released into the uterus. The disposable component does not include valves or fluid pumping means and can therefore be manufactured for minimal cost.

A further object of the invention is to automate balloon inflation and control of balloon inflation pressure. The described apparatus provides improved control of balloon inflation pressure by modulating pneumatic pressure within a chamber external to the patient. This pressure can be readily monitored and automatically controlled with a high degree of accuracy to achieve the desired inflation pressure of the distal balloon during the treatment period, adapting quickly to changes in uterine volume due to relaxation or contraction of the associated musculature. By using pneumatic pressure to transfer liquid from the proximal flexible balloon into the distal flexible balloon and withdraw liquid from the distal flexible balloon, the system achieves a high degree of control and reduces user errors.

Yet another object of the invention is to provide a physical means to indicate when the proper depth of insertion of the balloon is achieved. The described apparatus uses a soft rubber flange ("cervical tab") around the insertion catheter which is larger than the cervical opening. This prevents insertion of the catheter beyond a predetermined depth into the uterus. The apparatus is configured such that when the catheter is inserted until this cervical tab rests against the proximal cervical opening, the associated treatment balloon can deploy to treat the indicated range of uterine sizes and volumes. Before treatment, the operator confirms by examination that the uterine depth and volume fall within this predetermined range, then the operator simply inserts the balloon until the cervical tab rests against the cervix. The operator does not need to change the depth of insertion or manner of use for different patients. As a result, there is minimal risk of perforating the uterus and treatment methodology is greatly simplified for the user.

A further object of the invention is to provide a means of preventing any treatment to the cervical canal. This is achieved by a thermal insulating sheath, which surrounds the liquid delivery catheter. When the treatment balloon and liquid delivery catheter are inserted such that the cervical tab rests against the cervix, the insulating sheath located distal to the cervical tab is precisely positioned within the cervical canal. This sheath has thermal insulating capabilities, which limit the heat transfer between the liquid delivery catheter and the patient's cervix and prevents unwanted treatment of this area.

BRIEF DESCRIPTION OF THE DRAWINGS

FIG. 1a and FIG. 1b provide an overview of the embodiment of the invention. FIG. 1a shows the reusable and disposable components separately, FIG. 1b shows the invention with the disposable component installed in the reusable component.

FIG. 2 provides a detailed cross sectional view of the disposable component.

FIG. 3 shows a detailed cross sectional view of the pneumatic chamber and associated components of the distal end of the reusable component.

FIG. 4 shows a detailed cross section of the proximal end of the disposable component and the reusable component when the reusable component is installed such that it is ready for use.

FIG. 7a shows deployment of the distal end of disposable component during treatment of a 7 cm deep uterus which is the smallest indicated uterus for use of the preferred embodiment of the invention.

FIG. 7b shows deployment of the distal end of disposable component during treatment of a 12 cm deep uterus which is the largest indicated uterus for use of the preferred embodiment of the invention.

FIG. 8 shows an alternate embodiment of the device in which a heating element is contained within the distal balloon.

DETAILED DESCRIPTION OF PREFERRED EMBODIMENTS

Figure 5:
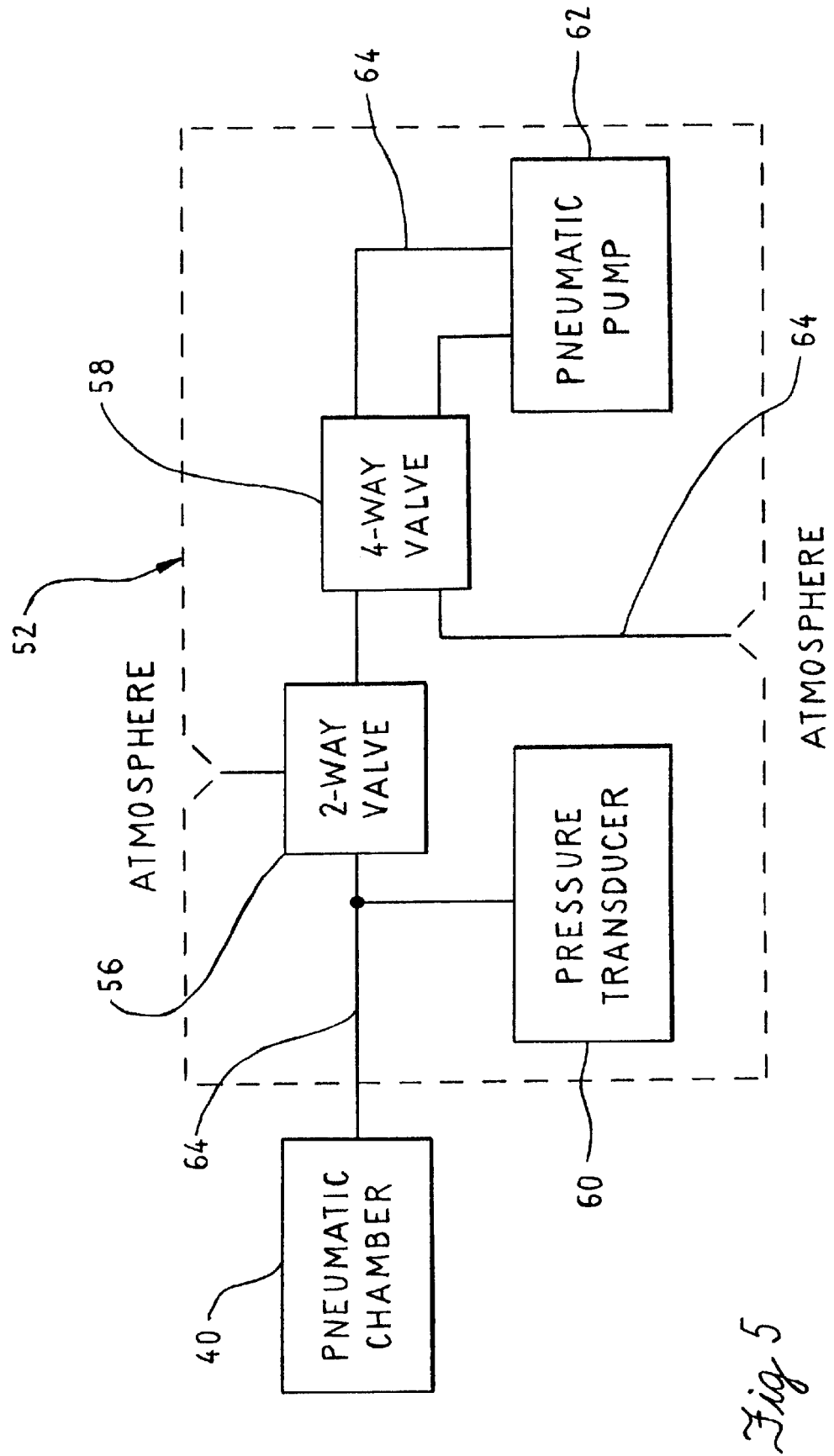
FIG. 5 provides details of the preferred embodiment of the pneumatic pressurizing means.

As shown in the drawings for the purposes of illustration, the present invention is embodied in a thermal balloon ablation apparatus which comprises a reusable component and a disposable component for delivering therapy to a body cavity.

In accordance with the present invention as shown in FIG. 1a and FIG. 1b, the thermal balloon ablation apparatus comprises a reusable component 2 and a disposable component 4. Reusable component 2 further comprises a housing 6 which has a handle 8. Integral to housing 6 is a display means 10 and user controls 12. Disposable component 4 comprises a distal balloon 14, a semi-rigid or rigid catheter 16 having a distal and proximal end, a semi-rigid or rigid distal sheath 18, a flange 20, a semi-rigid or rigid proximal sheath 22, a pneumatic fitting 24, a proximal balloon 26, and a protective shield 28.

FIG. 2 shows a detailed cross sectional view of disposable component 4. Distal balloon 14 can be inflated to volumes of 30 ml without generating significant back-pressure and is suitable for use at temperatures in excess of 165 C. In the preferred embodiment the balloon is fabricated from 0.12 mm thick silicone rubber, is shaped in the approximate shape of the uterine cavity and has a natural volume of approximately 15 ml, however other materials and shapes are acceptable so long as they allow the balloon to substantially conform to the uterus when inflated and provided they facilitate transfer of heat energy between the liquid contained in the balloon and the endometrium. Distal balloon 14 is bonded in a liquid tight manner to the distal end of catheter 16. In the preferred embodiment this bond is made using an adhesive material. The distal end of catheter 16 further includes a plurality of liquid ports 30 located such that they are contained within distal balloon 14. In the preferred embodiment, proximal balloon 26 is fabricated from silicone rubber and has a natural volume of approximately 30 ml. The proximal end of catheter 16 is bonded in a liquid tight manner to the proximal balloon such that a liquid tight system exists comprising distal balloon 14, catheter 16 and proximal balloon 26. In the preferred embodiment this bond is made using an adhesive material.

The liquid tight system comprising distal balloon 14, catheter 16 and proximal balloon 26 is filled with liquid 32 such that there exists only liquid 32 within the system and no significant volume of gas at room temperature and ambient pressure. Liquid 32 must be non-toxic and pose minimal hazard to the patient in the event that distal balloon 14 ruptures. Ideally, liquid 32 should be such that it can be heated to temperatures above 100 C. without boiling. In the preferred embodiment 100% Glycerin is used which can be heated to temperatures above 165 C. without boiling at ambient pressures. A total volume of approximately 30 ml of liquid 32 is contained within the system such that the entire volume of liquid can be contained within the natural volume of the proximal balloon 26 such that distal balloon 14 can be collapsed for insertion through the cervix.

The distal end of catheter 16 further includes an end cap 34 fabricated from a soft rubber material in order to reduce the risk of perforating distal balloon 14 or uterine tissue during insertion into the uterus. A thermal insulating material 36 is located between catheter 16 and distal sheath 18 and between catheter 16 and proximal sheath 22. Thermal insulating material 36 prevents excessive heating of the external surfaces of the distal sheath 18 and proximal sheath 22 during thermal balloon ablation treatment using the apparatus. In the case of distal sheath 18, it is desirable to ensure that the temperature of the external surface does not exceed 49 C. in order to prevent necrosis of tissues of the cervical canal, defined as the area between the internal opening (also known as "os") of the cervix and the external os of the cervix of a patient. In the preferred embodiment, thermal insulating material 36 is a combination of mica and closed cell silicone rubber foam. Distal sheath 18 has a diameter of approximately 6 mm such that it can be easily inserted through the cervical canal of a patient. Distal sheath 18 and proximal sheath 22 are separated by flange 20 which is of sufficient diameter that it cannot be inserted into the cervical canal of a patient. In the preferred embodiment, flange 20 is fabricated from silicone rubber and has a diameter of 12 mm. The dimensions of disposable component 4 are intended such that the distal end of the apparatus can be inserted through the cervical opening into the uterus to the point at which flange 20 prevents further insertion, to treat uteri with sounded depths between 7 cm and 12 cm as measured from the external cervical opening. Therefore the length of distal sheath 18 plus the length of catheter 16 protruding distally beyond distal sheath 18 is less than 7 cm. The dimensions of disposable component 4 are also intended to shield the cervical canal from treatment where the cervical canal is defined, for the purpose of this embodiment, as the 3.5 cm long region immediately internal to the external cervical opening, and therefore distal sheath 18 is approximately 3.5 cm in length. It will be obvious to one skilled in the art that these dimensions can be varied to suit the anatomy of the body cavity which is to be treated using the apparatus.

Proximal balloon 26 is covered by a protective shield 28 comprised of a rigid heat conducting material. In the preferred embodiment, this material is thin-walled aluminum with an outer diameter of approximately 2 cm and a length of approximately 10 cm. Any similar material or configuration is acceptable so long as it provides mechanical protection for proximal balloon 26 during handling and insertion into reusable component 2 and so long as proximal balloon 26 makes substantial contact with the inside surface of protective shield 28 when the total volume of liquid 32 is substantially contained within proximal balloon 26. Protective shield 28 is affixed to the proximal side of pneumatic fitting 24. Catheter 16 extends through pneumatic fitting 24 in an airtight manner. Pneumatic fitting 24 further includes a rubber O-ring 38 on its proximal surface.

It is necessary that all components of the apparatus which may come into contact with the vaginal canal, cervix or uterus be sterile at the time of use, non-toxic, and non-allergenic. It is intended that disposable component 4 is sterile and will be discarded after each use of the device to treat a single patient.

FIG. 3 shows a detailed cross sectional view of the pneumatic chamber 40 and associated components of the distal end of reusable component 2. Pneumatic chamber 40 further contains a cylindrical heating element 42 and an inner chamber 44. In the preferred embodiment, heating element 42 is a 60 watt, electrically powered, flexible membrane type heater. Inner chamber 44 is cylindrical in shape and approximately 2 cm in diameter and 11 cm in length such that is allows insertion of protective shield 28 and the proximal balloon 26 and liquid 32 contained therein. In the preferred embodiment pneumatic chamber 40 is fabricated from nylon material and inner chamber 44 is fabricated from stainless steel. Heating insulation 46 located around the outside of the heating element minimizes heat transfer from heating element 42 to the external surface of pneumatic chamber 40 and housing 6. A plurality of heater temperature sensors 48 are located on or adjacent to heating element 42 in order to produce a signal indicative of the temperature of heating element 42. A plurality of liquid temperature sensors 50 are located so as to be adjacent to proximal balloon 26 when it is located in pneumatic chamber 40 and substantially filled with liquid 32 in order to produce a signal indicative of the temperature of the liquid in proximal balloon 26. In the preferred embodiment heater temperature sensors 48 and liquid temperature sensors 50 are T-type thermocouples. Pneumatic chamber 40 is connected in an airtight manner to a pneumatic pressurizing means 52.

When the disposable component 4 is installed in reusable component 2, locking connectors 54 located on the distal end of pneumatic chamber 40 engage pneumatic fitting 24 such that rubber O-ring 38 is compressed between pneumatic fitting 24 and pneumatic chamber 40 providing an air tight seal. A disposable component detection means 55 is located on pneumatic chamber 40 and adjacent to locking connectors 54 which generates a signal when pneumatic fitting 24 is engaged on the distal end of pneumatic chamber 40. In the preferred embodiment disposable component detection means 55 is a mechanical contact switch having an actuator which generates an electrical signal when the actuator is depressed through contact with pneumatic fitting 24. Alternately, disposable component detection means 55 can be an electrical contact mechanism and may further include an electrical fuse arrangement in disposable component 4 in which the fuse is blown by applying an electrical current from reusable component 2 after the apparatus is used to treat a patient. This allows detection of cases in which the user installs a previously used disposable component 4 in which case the apparatus could be configured to inhibit further operation.

FIG. 4 shows a detailed cross section of the proximal end of disposable component 4 assembled within and reusable component 2. When installed in this manner, proximal balloon 26 is sealed within pneumatic chamber 40 in an air-tight manner. By modulating the pressure in pneumatic chamber 40 using pneumatic pressurizing means 52 the apparatus initiates flow of liquid 32 between proximal balloon 26 and distal balloon 14 through catheter 16 and liquid ports 30. For example, if a vacuum of −100 mmHg is maintained in pneumatic chamber 40 relative to ambient pressure, liquid 32 will be drawn from distal balloon 14 such that after a short period of time, substantially all of liquid 32 will be located in proximal balloon 26. Also for example, if a positive pressure of 180 mmHg is maintained in pneumatic chamber 40 relative to ambient pressure, liquid 32 will tend to flow from proximal balloon 26 into distal balloon 14. In this case, and when distal balloon 14 is located within an enclosed cavity such as the uterus of a patient, and when this enclosed cavity is less than 30 ml in volume, after a short period of time distal balloon 14 will reach a steady state in which a volume of liquid 32 is located in distal balloon 14 with a liquid pressure of 180 mmHg relative to ambient pressure.

FIG. 5 provides details of the preferred embodiment of pneumatic pressurizing means 52. In the preferred embodiment, pneumatic pressurizing means 52 comprises a solenoid activated 2-way, 2-position valve 56, a solenoid activated 4-way, 2-position valve 58, a pneumatic pressure transducer 60, a pneumatic pump 62 and flexible pneumatic tubing 64. The configuration shown in FIG. 5 allows pneumatic pressurizing means 52 to generate either positive or negative pneumatic pressure at an input port of 2-way, 2-position valve 56 by switching 4-way, 2-position valve 58 and operating pneumatic pump 62. The 2-way, 2-position valve 56 is switched to either connect pneumatic chamber 40 to this input port or alternately to connect pneumatic chamber 40 directly to atmosphere for rapid venting of air within pneumatic chamber 40. Pressure transducer 60 provides an output signal indicative of the pressure within pneumatic chamber 40 relative to ambient pressure and must be capable of measuring both positive and negative pressures. Pneumatic pump 62 is capable of start-up and operating over a range of pressures of at least −100 mmHg to +180 mmHg relative to ambient pressure. It will be understood by one skilled in the art that a variety of apparatus could be similarly utilized in order to act as pneumatic pressurizing means 52.

Figure 6:
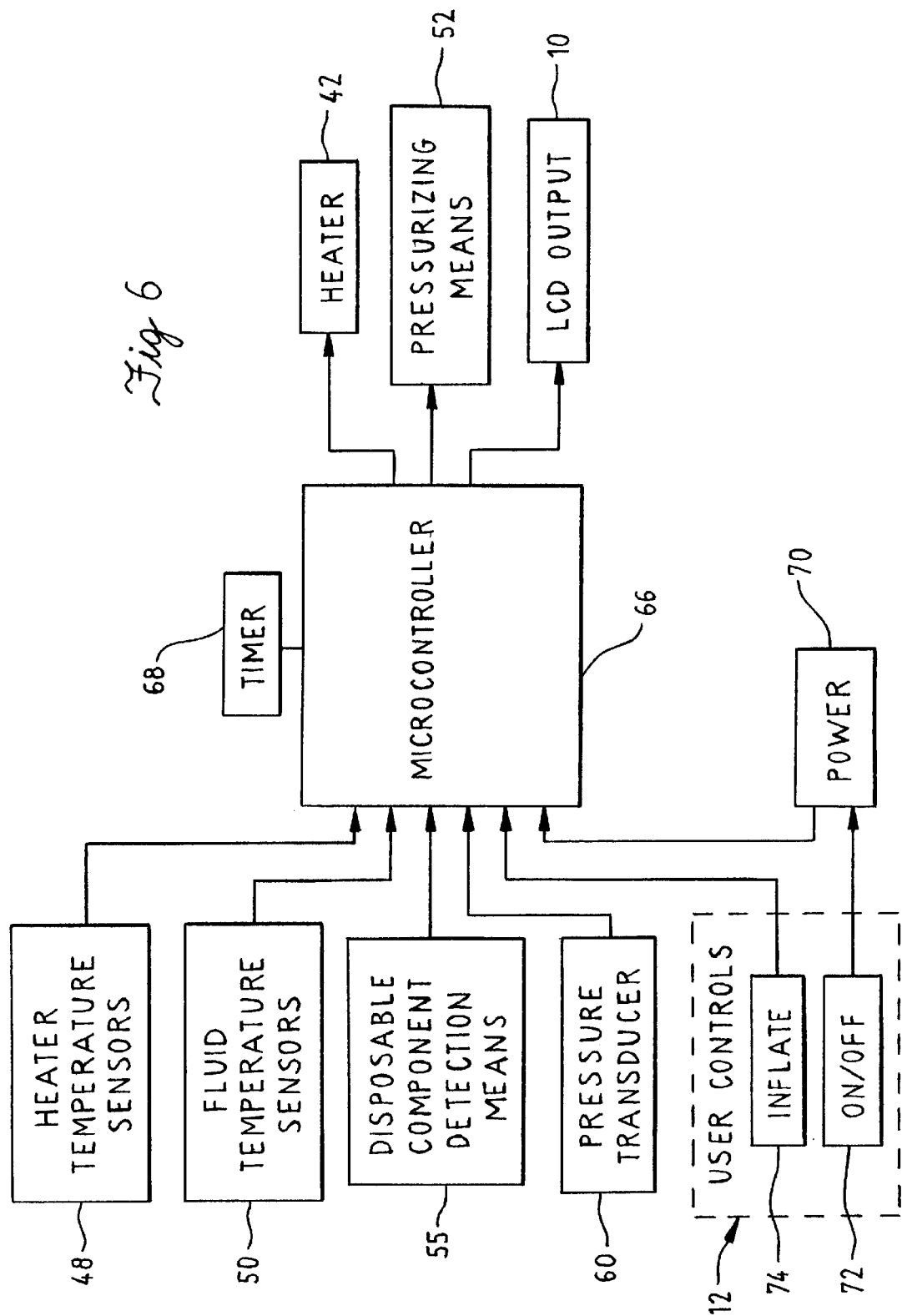
FIG. 6 shows details of the control system contained within the reusable component.

FIG. 6 shows details of the control system contained within reusable component 2. Re-usable component further comprises a microcontroller 66 with an integral timer 68, and an electrical power supply 70. In the preferred embodiment, display means 10 is an LCD module and user controls 12 comprise an on/off power switch 72 and an inflate switch 74. Microcontroller 66 accepts as inputs signals from heater temperature sensors 48, liquid temperature sensors 50, disposable component detection means 55, pressure transducer 60, and inflate switch 74. Microcontroller 66 has outputs which control operation of heating element 42, pneumatic pressurizing means 52 and display means 10. On/off power switch 72 provides a means for an operator to connect or disconnect microcontroller 66 and thereby all electrical components of the invention from electrical power supply 70 and thereby initiate or terminate operation of the apparatus.

In the preferred embodiment, microcontroller 66 operates to control operation of the system to allow a user to deliver thermal balloon ablation treatment to the uterine cavity of a patient. The user first activates the device by turning on-off power switch 72 to the "on" position. This provides power to microcontroller 66 which in turn provides power as required to all electrical components of the invention and initiates the software program which is resident in microcontroller 66.

Microcontroller 66 first acts to poll disposable component detection means 55 to determine if a disposable component 4 has been properly inserted and locked into reusable component 2. If no disposable component 4 is detected, microcontroller issues a notice to the user via display means 10 and continues to poll disposable component detection means 55. When a disposable component 4 is detected, operation of microcontroller 66 proceeds to pre-heat liquid 32.

Pre-heating liquid 32 involves the following steps. First pneumatic pressurizing means 52 is activated to draw and maintain a pneumatic pressure of approximately −100 mmHg relative to atmosphere in pneumatic chamber 40. This has the effect of drawing substantially all of liquid 32 into proximal balloon 26 which is sealed inside pneumatic chamber 40. Then, after a period of approximately 30 seconds, microcontroller activates heating element 42 and monitors the signals from heater temperature sensors 48 and liquid temperature sensors 50. A pressure of approximately −100 mmHg is maintained in pneumatic chamber 40 throughout the pre-heating of liquid 32. In the event that the temperature of heating element 42 exceeds 200 C. as indicated by heater temperature sensors 48, microcontroller turns heating element 42 off until the measured heater temperature drops below 165 C. This is to prevent excessive temperatures at the surface of heating element 42 from damaging proximal balloon 26. Pre-heating of the liquid is terminated when liquid temperature sensors 50 indicate that liquid 32 within proximal balloon 26 reaches a temperature of 165 C. In practice, pre-heating of liquid 32 typically requires about 5 minutes. During this pre-heating period, microcontroller 66 implements test routines in order to detect leaks or problems with the apparatus and proceeds to generate warnings to the user via user display 10 or inhibit further operation as warranted. These are not described but will be apparent to those skilled in the art. When pre-heating is terminated, the invention is ready for use to treat a patient.

When the invention is ready for use to treat a patient, microcontroller 66 outputs a suitable message via display means 10. Microcontroller 66 then operates pneumatic pressurizing means 52 to maintain a pressure of approximately −100 mmHg in pneumatic chamber 40 and operates to maintain liquid 32 within proximal balloon 26 at a temperature between 160 C. and 170 C. Maintaining the temperature of liquid 32 in this range is achieved by cycling heating element 42 on and off in response to signals from heater temperature sensors 48 and liquid temperature sensors 50 in a similar manner to that described during pre-heating of liquid 32. When the invention is ready to treat a patient, microcontroller 66 also monitors inflate switch 74 to determine when it is activated by the user.

When the invention is ready for use to treat a patient, the user inserts the distal end of disposable component 4 through the cervical opening of the patient until flange 20 rests against the cervix preventing further insertion. This operation precisely locates the distal balloon 14 and distal sheath 18 in the uterine cavity as required for treatment. It is expected that the patient has been prepared for surgery and may have received a sedative or anesthetic. It is also expected that the user will have confirmed that the depth and volume of the uterine cavity are suitable for use of the described invention. After the distal balloon 14 and associated components have been properly located in the patient, the user activates inflate switch 74 to begin treatment.

When microcontroller 66 detects activation of inflate switch 74, it proceeds to implement a treatment cycle as follows. First heating element 42 is turned off. Next, timer 68 is activated and pneumatic pressurizing means 52 releases the −100 mmHg vacuum in pneumatic chamber 40 to atmosphere through 2-way, 2-position valve 56. Pneumatic pressurizing means 52 is then activated to generate and maintain a pneumatic pressure of 180 mmHg in pneumatic chamber 40. This has the immediate effect of forcing 165 C. liquid 32 from the proximal balloon 26 through catheter 16 and liquid ports 30 into distal balloon 14 which is located in the uterus of the patient. After a short period of time, the liquid in distal balloon 14 reaches a steady state pressure of 180 mmHg. At this pressure, the uterus will be fully distended and distal balloon 14 will be filled with heated liquid 32 and be in contact with substantially all of the walls of the uterine cavity. In this steady state, the liquid pressure inside distal balloon 14 will be essentially equal to the liquid pressure inside proximal balloon 26 and the pneumatic pressure inside pneumatic chamber 40. The microcontroller operates to automatically maintain this pressure in pneumatic chamber 40, and thereby distal balloon 14 for a period of 90 seconds as indicated by timer 68. During this 90 second period thermal energy from heated liquid 32 within distal balloon 14 is dissipated to the surrounding tissue of the uterus and results in the desired cauterization of the endometrial tissue. During this 90 second period, the temperature of liquid 32 in distal balloon 14 will decrease as the heat energy is dissipated to the surrounding tissues. The nature of this cooling will be dependent of the specific anatomy of the uterine cavity undergoing treatment. In some cases in order to minimize this cooling effect it may be advantageous for microcontroller 66 to pulse the pneumatic pressure in pneumatic chamber 40 during the treatment period in order initiate flow back and forth between distal balloon 144 and proximal balloon 26 to continually mix the volume of heated liquid 32 contained within disposable component 4.

When the 90-second treatment period is completed, microcontroller 66 proceeds to control operation of the invention as follows. First, timer 68 is reset and pneumatic pressurizing means 52 releases the 180 mmHg pressure in pneumatic chamber 40 to atmosphere through 2-way, 2 position valve 56. Pneumatic pressurizing means 52 is then activated to generate and maintain a pneumatic pressure of approximately –100 mmHg in pneumatic chamber 40. This has the immediate effect of withdrawing liquid 32 from distal balloon 14 back into proximal balloon 26 through catheter 16 and liquid ports 30. After 15 seconds as indicated by timer 68, microcontroller 66 generates a message to the user via display means 10 indicating that distal balloon 14 has been deflated and can be removed from the uterus of the patient. It is expected that the user will then remove the apparatus from the patient.

After another 120 seconds as indicated by timer 68, microcontroller 66 operates to vent pneumatic chamber 40 to atmosphere through 2-way, 2 -position valve 56 and generates a message to the user via display means 10 indicating that the user can remove and discard disposable component 4. Microcontroller 66 then monitors disposable component detection means 55 in order to detect when disposable component 4 is removed from reusable component 2 for discard. When removal is detected microcontroller 66 continues to poll for installation of a new disposable component 4 in order to allow another patient to be treated or the invention can be turned off by the user using on/off power switch 72.

The described operation of the invention is for illustration purposes only. It will be obvious to one skilled in art that there are numerous possible modifications to the operation of the invention as described.

FIG. 7a shows deployment of the distal end of disposable component 4 during treatment of a 7 cm deep uterus which is the smallest indicated uterus for use of the preferred embodiment of the invention. FIG. 7b shows deployment of the distal end of disposable component 4 during treatment of a 12 cm deep uterus which is the largest indicated uterus for use of the preferred embodiment of the invention. The outlines of distal balloon 14 prior to inflation 76 and after inflation 78 with liquid 32 to a pressure of 180 mmHg. This shows how the invention operates to treat the indicated range of uterine sizes after inserting disposable component 4 through the cervical canal until flange 20 prevents further insertion. When the user properly operates the device by inserting disposable component 4 through the cervical opening and into the uterus of a patient in this manner, the invention does not require a user to adjust insertion depth based on uterine length, minimizing the risk of perforating the uterus, and providing thermal protection of the cervical canal by ensuring distal sheath 18 and the underlying thermal insulating material 36 are properly located between the internal os and external os of the cervix.

FIG. 8 shows an alternate embodiment of the device. In this alternate embodiment, heating element 42, and one or more of liquid temperature sensors 50 are located within distal balloon 14. This embodiment further includes a multi-conductor electrical cable 80 and an electrical connector 82 which operates to make electrical contact when pneumatic fitting 24 is engaged by locking connectors 54. Multi-conductor electrical cable 80 and electrical connector 82 function in order to provide power from electrical power supply 70 to heating element 42 and to control operation of said heating element 42 via operation of microcontroller 66. Multi-conductor electrical cable 80 and electrical connector 82 also function to convey signals from liquid temperature sensors 50 indicative of the liquid temperature within distal balloon 14 to microcontroller 66. In the alternate embodiment, heating element 42 is a liquid-tight, 40 W, electrical resistance type heater and liquid temperature sensors 50 are T-type thermocouples.

Operation of the alternate embodiment differs from the preferred embodiment in that liquid 32 is not heated prior to initiation of treatment, but is instead heated after distal balloon 14 is inserted through the cervical opening into the uterus and inflated to a pressure of 180 mmHg by pneumatic pressurization of pneumatic chamber 40. When the user initiates treatment by pressing inflate switch 74, microcontroller 66 operates to inflate distal balloon 14 as described in the preferred embodiment then operates control heating element 42 to heat the liquid within the distal balloon to a pre-determined temperature as indicated by liquid temperature sensors 50. In the alternate embodiment microcontroller 66 maintains said liquid temperature for a predetermined time as measured by timer 68 before withdrawing the liquid into the proximal balloon 26 by operating pneumatic pressurizing means 52 to draw a negative pressure in pneumatic chamber 40. In this alternate embodiment it is desirable that liquid 32 be of a viscosity such that it readily flows through catheter 16 and liquid ports 30 for inflation of distal balloon 14. For example, saline solution can be used as liquid 32, in which case heating of the liquid is restricted to temperatures substantially below 100 C. to prevent boiling. In the alternate embodiment and using saline solution as liquid 32 a liquid temperature of approximately 85 C. and a treatment time of approximately 10 minutes have been found effective to cauterize the endometrium. Use of other liquids with low viscosity and higher boiling points, such as perfluoroperhydrophenanthrene (C14F24) allows use of higher treatment temperatures and shorter treatment times.

It will be appreciated by one skilled in the art that a variety of alternate embodiments exist for the disclosed inventions which may also specifically include a combination of the two described embodiments such that heating of liquid 32 is initiated by heating elements located in both reusable component 2 and disposable component 4. Specifically this combination would be advantageous where it is desired to locate heating element 42 in distal balloon 14, however, liquid 32 is highly viscous and must be heated above ambient temperature by a heating element external to distal balloon 14 in order to adequately flow through catheter 16 and liquid ports 30 for inflation of distal balloon 14. For example, this allows use of 100% Glycerin as the liquid 32, which is highly viscous at room temperature but can be heated to temperatures of over 165 C. without boiling.

It will also be recognized that the described apparatus could readily be modified by replacing heating element 42 with a cooling means in order to enable injection of cold liquid into distal balloon 14 to cauterize the endometrium. Similarly it will be understood by one skilled in the art that the disclosed apparatus could readily be modified to effect thermal balloon ablation of other cavities or ducts in the human body, such as the urethra for treatment of pathological conditions of the prostate gland.

It will be apparent from the foregoing that, while particular forms of the invention have been illustrated and described, various modifications can be made without departing from the spirit or scope of the invention. Accordingly, it is not intended that the invention be limited except as by the appended claims.

What is claimed is:

1. A device for causing necrosis of tissue comprising:
   a liquid-tight system having a distal flexible member; a proximal flexible member; and a catheter joining and providing a liquid path between said distal and proximal members, the system containing a liquid;
   a pneumatic chamber into which the flexible proximal member may be inserted;
   a means to controllably heat the contents of the pneumatic chamber and thereby heat the liquid in the flexible proximal member; and
   a means to apply variable pneumatic pressure to the pneumatic chamber to initiate liquid flow between the distal member and the proximal member.

2. An apparatus according to claim 1 where said means to apply variable pneumatic pressure includes a pneumatic pump, a pneumatic valve and a pressure transducer.

3. An apparatus according to claim 1 where the means to controllably heat the contents of the pneumatic chamber comprises an electrically controllable heater and a plurality of temperature sensors.

4. An apparatus according to claim 3 where one or more of the temperature sensors are located adjacent to the proximal member when said proximal member is sealed inside the pneumatic chamber such that said temperature sensors generate an output signal indicative of the temperature of the liquid within the proximal member.

5. An apparatus according to claim 1 where said controlling means further operates the apparatus to:
   (a) first draw substantially all of the liquid into the proximal member by applying and maintaining a negative pressure in the pneumatic chamber such that the distal member contains minimal liquid;
   (b) while maintaining this negative pressure in the pneumatic chamber, operate the means to heat the contents of the pneumatic chamber in order to heat the liquid within the proximal member to a pre-determined temperature;
   (c) then inject a volume of the heated liquid into the distal member by applying a positive pneumatic pressure to the pneumatic chamber;
   (d) then modulate the pressure in the pneumatic chamber such that the heated liquid is held in the distal member at a pre-determined pressure for a predetermined time; and
   (e) after said predetermined time withdraw the liquid from the distal member into the proximal member by applying a negative pressure to the pneumatic chamber.

6. An apparatus according to claim 1 wherein the liquid within the liquid tight system is such that it can be heated to temperatures in excess of 100 degrees Celsius at sea level without boiling.

7. An apparatus according to claim 1 where said catheter joining and providing a liquid path between said distal and proximal members includes a surrounding sheath of thermal insulating material covering a portion of the catheter where the sheath has a proximal and distal section which are separated by a flange of sufficient diameter such that it cannot be inserted through the cervical opening.

8. A device for facilitating necrosis of tissue comprising:
   a distal flexible bladder;
   a proximal flexible bladder;
   a catheter joining said distal and proximal flexible bladders in a liquid tight system,
   a liquid inside the system to flow between the two bladders; wherein the liquid is in amount that permits the distal member to substantially deflate when the liquid is moved out of the distal end and wherein the liquid is of a type wherein the liquid viscosity substantially decreases when heated;
   a connector for connecting the device to a pressurizing source; and
   a means to heat the liquid in order to reduce the viscosity of the liquid.

9. A method for causing necrosis of a the tissue in a body cavity comprising the steps of:
   inserting a first bladder into a body cavity where said first bladder is in liquid communication with a second liquid filled bladder and preheating the liquid contained in said second bladder to a known temperature;
   forcing the heated liquid contained within said second bladder into said first bladder contained in the body cavity;
   maintaining the heated liquid in said first bladder for a predetermined time to dissipate heat energy to the tissues of the surrounding body cavity; and
   after said predetermined time, drawing the liquid contained in said first bladder back into said second bladder, thereby allowing removal of said first bladder from the body cavity.

10. A method as described in claim 7 in which step (d) further includes heating the liquid contained in the first bladder using a heat releasing element located in the first bladder.

* * * * *